United States Patent [19]

Kim

[11] Patent Number: 4,705,041

[45] Date of Patent: Nov. 10, 1987

[54] DILATOR FOR SPHINCTER OF ODDI

[76] Inventor: Il G. Kim, N. Main St., Hughesville, Pa. 17737

[21] Appl. No.: 910,154

[22] Filed: Sep. 19, 1986

Related U.S. Application Data

[63] Continuation-in-part of Ser. No. 628,649, Jul. 6, 1984, abandoned.

[51] Int. Cl.⁴ ............................................ A61M 29/00
[52] U.S. Cl. .................................................... 128/343
[58] Field of Search .................. 128/1 R, 303 R, 345, 128/325, 344, 341, 343; 604/104, 105, 106

[56] References Cited

U.S. PATENT DOCUMENTS

| | | | |
|---|---|---|---|
| 2,230,226 | 2/1941 | Auzin | 604/104 |
| 3,196,876 | 7/1965 | Miller | 128/343 |
| 3,241,554 | 3/1966 | Coanda | 128/345 X |
| 3,633,565 | 1/1972 | McDonald | 128/304 X |

Primary Examiner—Michael H. Thaler
Attorney, Agent, or Firm—Anthony J. Dixon

[57] ABSTRACT

Apparatus and process for dilating the Sphincter of Oddi comprising a flexible cylindrical catheter with an expandible tip to allow verification of its location by outside palpitation and a plurality of hollow flexible dilators which are slidingly inserted coaxialy over the catheter to stretch the Sphincter to the desired extent, each dilator comprising an enlarged tip portion, a shaft portion and a tail or handle portion finned to accommodate the user.

8 Claims, 7 Drawing Figures

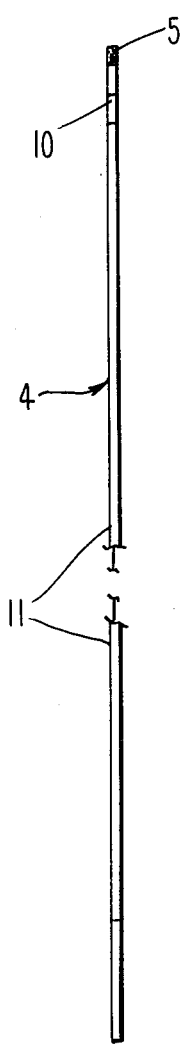
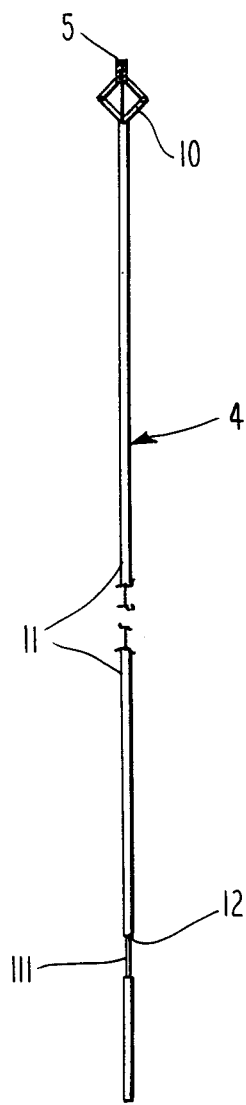
Fig. 2A
Fig. 2B
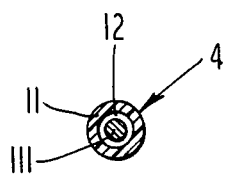
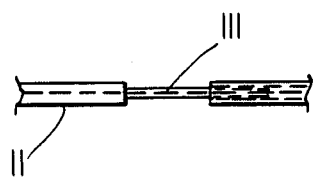
Fig. 2C
Fig. 2D

DILATOR FOR SPHINCTER OF ODDI

This is a continuation-in-part of application Ser. No. 628,649, filed July 6, 1984, now abandoned.

BACKGROUND OF THE INVENTION a. Field of the Invention

The present invention relates to the class of surgical instruments and processes.

More particularly, it relates to instruments used in the dilation of the Sphincter of Oddi often done in treatment of common bile duct pathological conditions such as stones and stricture.

More particularly, it relates to an improved catheter and dilator device for dilation of the Sphincter without the risk of excessive and life threatening trauma in present devices.

On many occasions, the common duct is opened to search for and remove stones. Certain indications for exploration of the common duct have been devised and whenever one or more of these indications are present, the duct is most often explored. Some of the common indications are: when a stone is palpable in the common duct; when the common duct is dilated; when there are small stones present in the gallbladder; when jaundice of the obstructive variety is present and various others. After the common duct has been opened and explored for stones, it is necessary to dilate the Sphincter of Oddi. This is done to encourage and facilitate passage of residual stones or debris left in the common duct. The Sphincter is also dilated to make sure that there is no stricture of the Sphincter of Oddi or stone present in the ampulla.

The usual procedure in this type of operation has been to make a longitudinal incision in the anterior surface of the common duct just distal to the entrance of the cystic duct for the entrance of the probe. The usual probe used for this purpose comprised a malleable metal rod approximately fifteen inches in length and having a portion approximately twice the length of the probe portion and an enlarged portion at the end of the probe portion. The probe is passed through the incision with the probe shaped to fit the curve of the common duct and its enlarge tip forced through the Sphincter of Oddi into the duodenum, thereby dilating the Sphincter of Oddi. To increase the dilation it has been customary to provide a plurality of probes, each having an increasingly larger tip, and successively inserting and removing the various probes.

The preceding steps not only increase the time of the probing operation due to the fact that each probe must be separately shaped to fit the curve of the common duct, but the insertion of the various probes increases the danger of tearing the common duct or pushing a hole in a portion of the common duct in an area not visible to the operator.

b. The Prior Art

An improvement to the above procedure and devices has been discussed by Maurice Miller in U.S. Pat. No. 3,196,876 issued July 27, 1965.

Miller discloses a one piece probe with a malleable lead portion and an enlarged oval tip which is manipulated through the Sphincter of Oddi. Then a number of incrasingly larger sleeves are threaded there over to enlarge and dilate the Sphincter. There are grave disadvantages to the system of Miller.

Firstly, it is time consuming and traumatice to bend stiff metallic dilators and identifying the proper location of the tip by outside manipulation.

Furthermore, the sharp rigid metallic tip of Miller's probe poses a high risk of creating peroration and false passage to the blinded portion of the distal common duct and also to the pancreas, leading to serious life threatening complications from digestive pancreatic enzymes.

Miller's probe tip is small and sharp as compared to Bake's dilator (1937 model) which is very popular among surgeons presently. It (Miller's) poses an unsureness of the passage of the Sphincter by palpation from outside of the duodenum. It is very difficult to identify whether it passed through the Sphincter opening or just invaginated (tenting). The unsure and potentially wrong location of Miller's probe followed by a series of Miller's malleable sleeve dilators can lead to the bursting of the blinded area of the distal common duct wall and may also lead to serious damage to the head of the pancreas.

Also, Miller's graduated dilator is made of a metallic malleable encircled type metal as illustrated and is not as flexible as compared with plastic material to follow the curved contour of the common duct. It also has the disadvantage of having to be manually bent to adjust to the contour of the common duct prior to introduction.

Lastly, Miller's sleeve dilator does not have a handle to grip for control and transmission of force to the dilator tip; and the small openings of the metallic dilators make cleaning and sterilizing difficult leading to unsureness of sterilization.

Another dilating apparatus previously discussed is that of Leland C. Gravlee in U.S. Pat. No. 3,811,449 issued May 21, 1974.

Gravlee discloses an apparatus which comprises an elongated flexible probe of uniform diameter and a dilator which slides thereover with further increasing diamter dilators sliding thereof.

A similar method has been used to dilate the Sphincter of the esophagus anus and cervical canal.

Since Gravlee's probe is less than three millimeteres in diameter, it is impossible for the surgeon to determine the proper location of the tip by outside palpitation. This can result in the tip being in the wrong location causing damage to the duct wall. Secondary damage to the pancreas might also occur.

Also, the primary probe might easily lead to invagination of the Sphincter of Oddi (tenting) into the duodenum instead of passing through the Sphincter opening and may lead to dilation of the wrong area.

Gravlee mentions an advantage of medical instrumentation through his dilator. There is no reason to insert such an instrumentation through the curved common duct. It is impossible to see the distal part of the common duct through such a small caliber of any opening of a dilator to perform a surgical procedure. There are much better and safer procedures to perform removal of a stone and biopsy. Sphincters should not be dilated more than six mm in diameter, (many doctors state that higher dilation will result in more stricture formation in the future except for unusually large dialted common ducts). It is practically impossible to perform biopsies or remove stones using Gravlee's instrument due to the curvature of the common duct and the small lumen.

SUMMARY OF THE INVENTION

An apparatus and process has now been devised which overcomes these and other problems in the art.

It is therefore an object of the present invention to provide a dilating apparatus utilizing a flexible plastic disposable instrument with graduated dilators.

It is a further object of the present invention to provide a device which reduces the amount of manipulation, trauma and handling of the duct during exploration.

It is a further object of the present invention to reduce operating time in this type of surgery.

It is a further object to insure absolute steralization.

It is a further object of the invention to provide an apparatus and process which allows treatment of common pathological conditions in the bile duct and Sphincter of Oddi while eliminating risk of damage to the duct wall and pancreas.

These and other objects and advantages of the invention can be achieved by the present dilating apparatus which comprises:
a. a hollow, flexible cylindrical catheter;
b. a soft insertion tip member fixedly attached to the leading end of said catheter;
c. an expandible member mounted axially adjacent to said tip and communicating with the interior of said catheter;
d. means for expanding the member of (c) whereby the location of the tip can be ascertained, and;
e. a plurality of hollow, flexible dilators with outer diameters of increasing size and with an inner diameter accommodatingly larger than the outer diameters of said catheter, each dilator having an enlarged tip portion on one end and a handle portion on the other end;

whereby dilation of the Sphincter is accomplished by insertion of the catheter until the tip is within the duodenum and subsequent insertion of the dilators one at a time slidingly over the catheter (in coaxial position in relation thereto) until the desired opening is achieved at which time the dilator and catheter are removed.

Thereafter, the necessary surgical procedures to complete the operation are performed.

Also disclosed is a scissor-like, expandible tip for use in the apparatus and process of the present invention.

Further advantages and understanding of the invention will become clear upon review of the attached drawings and description of the preferred embodiment which follows.

BRIEF DESCRIPTION OF THE DRAWINGS

FIGS. 2a and 2b is a fragmented view of expanded catheter tip.

FIG. 2c is a cross-sectional view of the catheter diameter.

FIG. 2d is a sectional view of the catheter illustrating the expansion of the tip.

THE PREFERRED EMBODIMENT

Figure 1:
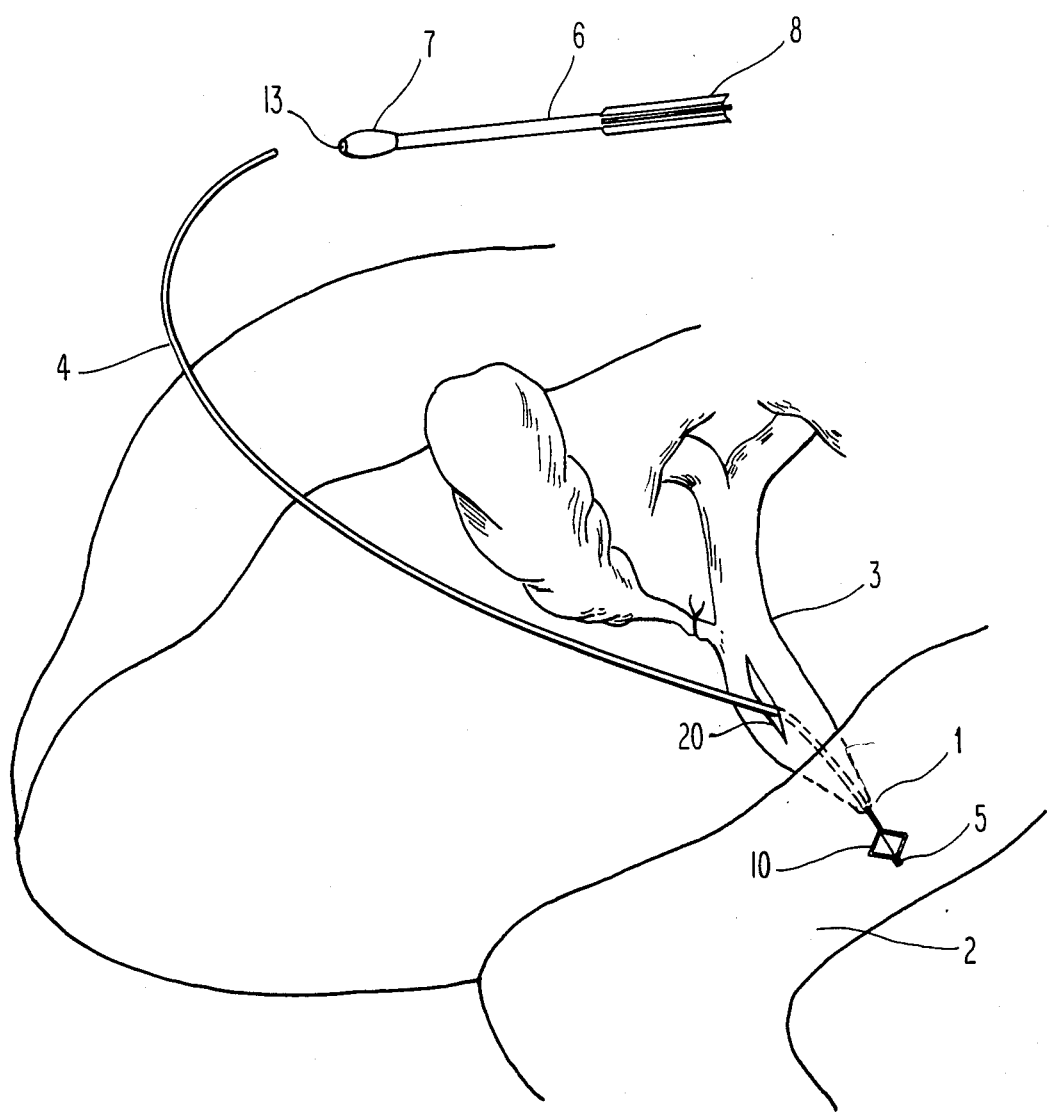
FIG. 1 is a schematic view of the duct, Sphincter of Oddi and duodenum with catheter inserted.

With reference to FIG. 1, a schematic depiction of the proposed surgical procedure utilizing the apparatus of the present invention can be readily understood.

The problem being corrected is a dilation of the Sphincter of Oddi as shown in FIG. 1. A catheter with an expandible tip, or guide catheter is shown in FIGS. 2a and 2b. In FIGS. 2a and 2b the guide catheter is a hollow member with an interior passageway, 12 within the passageway is located means for expanding the member, 10. This is accomplished by inflation of a pneumatic device or balloon or by a scissor-like member as shown. In the second instance, the member, 10 is expanded by a pulling action on a wire, 111 on the other end of the catheter. (See FIG. 2d). This causes the member, 10 which pivots in the scissor-like fashion shown, to expand. Catheter, 4 is reached into the duodenum, 2 through incision, 20 in the duct, through duct 3, through Sphincter, 1. The guide catheter member, 10 is expanded through the scissor-like action to insure that the catheter soft tip, 5 is in the proper location. This is easily accomplished by palpitation of the expanded member, 10 from outside the duodenum and pulling back the catheter soft tip, 5 toward the opening of the common duct to insure the proper location. If the soft tip, 5 is not where desired, the member, 10 can be collapsed by deflation or pushing the wire insert, 111 to collapse the scissor pivot and the guide catheter can be withdrawn without undue force for identification.

In one embodiment the member, 10 is constructed by forming three longitudinal slits in the wall of the catheter and fixing wire, 111 to tip, 5. By pulling the outside end of wire, 111 soft tip, 5 is pulled back causing the pivot action of the catheter material to form the expanded member, 10.

Figure 3:
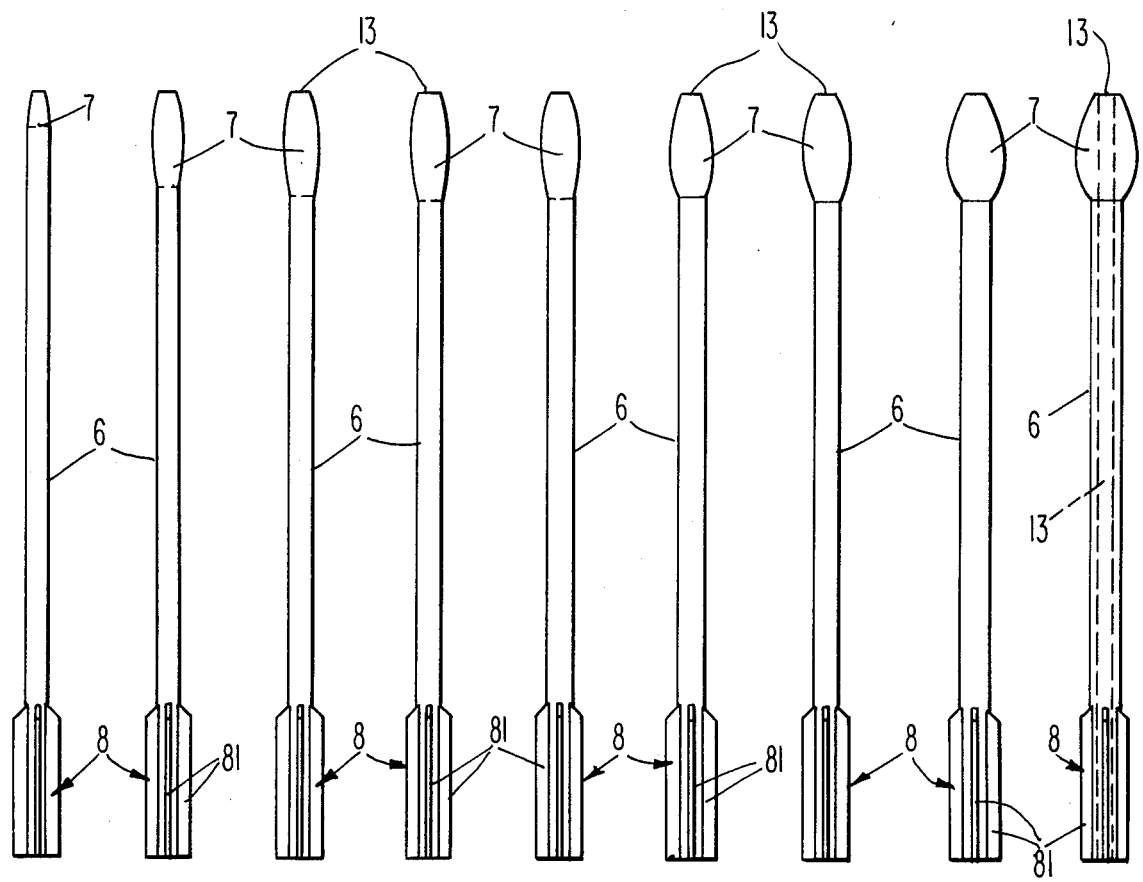
FIG. 3a is a full view of the dilator of 3 mm to 11 mm sizes.

When this is accomplished, the flexible dilators (FIG. 3) can be slid over the guide catheter and through the Sphincter. Increasingly larger dilators are inserted and removed until the desired opening is achieved. (See FIG. 3a).

The flexibility of the dilator, 6 is most advantageous since it follows the curvature of the duct and acts as a guide for determining the amount of force transmitted to the dilator tip, 7.

Figure 4:
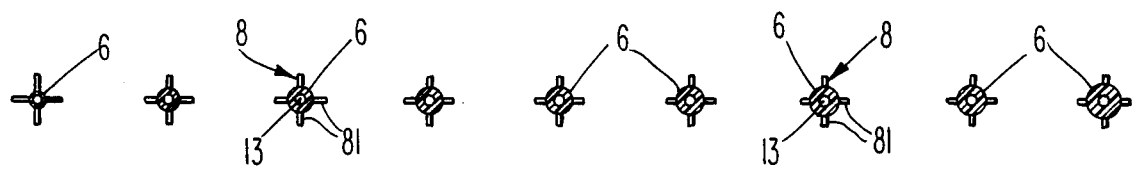
FIG. 4 is a cross-sectional view of the catheter.

FIG. 3a depicts larger dilators and shows the enlarged tip area, 7 more clearly. Also depicted is the tail section, 8 which the surgeon grips. Each dilator has an interior diameter, 13 (see FIG. 4) which is accommodatingly larger than the exterior diameter of catheter shaft, 11 to allow it to slide easily into the area being treated.

The catheters are available in the art at present and are of the following dimensions:

| | |
|---|---|
| overall length | 300 mm |
| handle length | 20 mm |
| tip length | 13 mm |
| diameter | 1½ mm |

Although not critical, these dimensions are normal in the art and recommended since the catheter should be accommodatingly smaller in diameter through the Sphincter of Oddi.

The dilators proposed which, together with the catheter, complete the present apparatus, are in graduated sizes. Length is about 125 mm overall with the tail section at about 25 mm which varies with tip size as follows:

| Tip width | Shaft Width |
|---|---|
| 3 mm | 3 mm |

| Tip width | Shaft Width |
|---|---|
| 4 mm | 3¼ mm |
| 5 mm | 3½ mm |
| 6 mm | 3¾ mm |
| 7 mm | 4 mm |
| 8 mm | 4 mm |
| 9 mm | 4¼ mm |
| 10 mm | 4¼ mm |
| 11 mm | 4½ mm |

The handle portion or tail portion, 8 of each dilator is constructed by four radially mounted fins, 81 flush at the end and tapered into the shaft toward the end of the fins. (See FIGS. 3 and 4). The length is about 25 mm.

Although these dimensions are not critical they are suggested in order to accommodate the average user, that is, the surgeon.

Thus, the apparatus and process as set forth herein is adapted to accomplish the objects and advantages described herein.

While a preferred embodiment of probe and dilator is described herein, it is to be understood that various alterations, changes and modifications are possible and may be made without departing from the scope of the present invention.

I claim as my invention:

1. An apparatus for dilation of the Sphincter of Oddi comprising
   a. a hollow cylindrical catheter at a diameter accommodatingly smaller than the Sphincter of Oddi;
   b. a soft insertion tip member mounted on said catheter;
   c. an expandible member mounted axially adjacent to said tip member and in communication with the interior of the catheter;
   d. means for expanding said expandible
   e. a series of hollow, flexible dilators of increasing outer diameter each with an inner diameter, said inner diameter accommodatingly larger than the outer diameter of the catheter, each dilator having an enlarged hollow tip portion on one end and a handle portion on the other end;
   whereby dilation occurs by insertion of the catheter until the tip is in the desired location and subsequent insertion of the dilators one at a time stepwise in order of increased outer diameter coaxially over the catheter until the desired dilation is achieved whereupon the dilator and catheter apparatus is removed.

2. The apparatus of claim 1 wherein the catheter is a guide catheter.

3. The apparatus of claim 1 wherein the catheter and dilators are constructed of flexible plastic.

4. The apparatus of claim 3 wherein the catheter has a length of about 300 millimeters, the dilators each having a lenth of about 125 millimeters and a width at the enlarged tip of from about 3 millimeteres to about 11 millimeters.

5. The apparatus of claim 4 wherein the dilator handle portion further comprises four radially mounted fins of a length of about 25 millimeters.

6. The apparatus of claim 5 wherein the means (d) for expanding said tip member further comprises a flexible wire communicating along the length of the hollow catheter and wherein the expandible member (c) is a pivotally mounted scissor-like member attached to the flexible wire which expands when the flexible wire is pulled and contracts when the flexible wire is pushed.

7. The process for dilation of the Sphincter of Oddi comprising:
   a. insertion of a hollow, cylindrical catheter; having a soft tip member, an expandible member mounted axially adjacent to the tip member and in communication with the interior of the catheter, and having a catheter diameter smaller than the Sphincter of Oddi's until the tip passes through the Sphincter;
   b. expanding the expandible member;
   c. verifying the tip location by palpitation;
   d. sliding a first, flexible, hollow dilator over the catheter until it passes through the Sphincter thereby dilating the Sphincter;
   e. removing the first dilator and successively inserting and removing dilators of increasing exterior diameter thereby dilating the Sphincter until the desired dilation is achieved; and
   f. removing the catheter thereby completing the process.

8. The process of claim 7 wherein the expandible member comprises a pivotally mounted scissor-like member which is expanded by action of a flexible wire slidingly inserted into the hollow catheter.

* * * * *